United States Patent [19]

Stefan-Dogar

[11] Patent Number: 5,040,982

[45] Date of Patent: Aug. 20, 1991

[54] DENTAL IMPLANT AND CONVERSION ASSEMBLY

[76] Inventor: Sorin Stefan-Dogar, 1610 NW 118th Ter., Pembroke Pines, Fla. 33026

[21] Appl. No.: 547,607

[22] Filed: Jun. 28, 1990

[51] Int. Cl.$^5$ ............................................. A61C 13/28
[52] U.S. Cl. .................................... 433/169; 433/173
[58] Field of Search .............. 433/169, 173, 174, 175, 433/176, 201.1

[56] References Cited

U.S. PATENT DOCUMENTS

| | | | |
|---|---|---|---|
| 3,934,347 | 1/1976 | Lash et al. | 433/173 |
| 3,991,472 | 11/1976 | Lukesch | 433/169 |
| 4,324,550 | 4/1982 | Reuther et al. | 433/169 |
| 4,488,874 | 12/1984 | Soifer | 433/173 |
| 4,552,532 | 11/1985 | Mozsary | 433/173 |
| 4,622,010 | 11/1986 | Koch | 433/173 |
| 4,746,293 | 5/1988 | Lundgren et al. | 433/173 |
| 4,756,689 | 7/1988 | Lundgren et al. | 433/173 |
| 4,772,204 | 9/1988 | Söderberg | 433/174 |
| 4,850,870 | 7/1989 | Lazzara et al. | 433/173 |
| 4,927,363 | 5/1990 | Schneider | 433/169 |
| 4,938,693 | 7/1990 | Bulakiev | 433/169 |
| 4,950,161 | 8/1990 | Richter | 433/173 |
| 4,957,437 | 9/1990 | Shimura et al. | 433/169 |

OTHER PUBLICATIONS

Int. J. Oral Surg. 1981: 10:387–416; Review Article, R. Adell et al.; "A 15-Year Study of Osseointegrated Implants in the Treatment of the Edentulous Jaw".

"The Nobelpharma Implant System", developed by Dr. P. I. Branemark, Advanced Training; Technician and O.R. Nurse Training.

"The Nobelpharma Implant System", developed by Dr. P. I. Branemark, Nobelpharma; Training Courses; Surgical Procedures; Prostetic Procedures.

Core-Vent Corporation, "The Story of Dental Implants", 1988.

Core-Vent Corporation, "IMZ Intramobile Stress-Abosrbing Element: Rationale vs. Reality"; Letter to the Editor, Dental Management.

Primary Examiner—John J. Wilson
Attorney, Agent, or Firm—Herbert L. Lerner; Laurence A. Greenberg

[57] ABSTRACT

In a dental implant assembly including a lower section having an implant fixture being disposed in a jaw-bone; the implant fixture having a threaded hole formed therein; a central section having an abutment screw screwed into the threaded hole; and an upper section attached to the abutment screw, an apparatus for resiliently supporting the upper section and sealing the abutment screw against the implant fixture, comprising a cylinder surrounding the abutment screw, and a bushing surrounding the abutment screw between the cylinder and the implant fixture.

18 Claims, 4 Drawing Sheets

DENTAL IMPLANT AND CONVERSION ASSEMBLY

BACKGROUND OF THE INVENTION

1. Field of the Invention

The invention relates to a dental implant and conversion assembly, and in particular to an improvement in the shock absorption and force distribution qualities of the dental implant assembly in the section of the assembly which is located between the gum line and the jaw-bone. The invention further relates to a conversion assembly for converting various types of implants for use with the assembly according to the invention.

2. Description of the Prior Art

Dental implants have become very popular in recent years as the modern method for replacing missing teeth, often eliminating the need for extensive bridge work or even dentures. Partial dentures can very easily be replaced by structures supported on implants. It is also known, in partially edentulous situations, to support a bridge on an implant and a natural tooth.

Implant surgery usually entails the following procedures: Firstly, an incision is made in the gum tissue, and the jaw-bone is revealed. Secondly, a hole is drilled in the jaw-bone. This may be done with a dental drill, at a drilling speed which ensures that the surrounding bone tissue is not damaged. Thirdly, an implant fixture is screwed into the hole in the jaw-bone so that its top is approximately flush with the jaw-bone. Such fixtures are usually made of titanium, and various lengths and diameters are commercially available.

After a period of several months, during which the implant fixture is allowed to osseointegrate with the jaw-bone tissue, the dental technician or dentist attaches certain other components of the assembly, such as an abutment section which extends substantially through the buccal mucoperiosteum, i.e. from the jaw-bone to the gum line. A dental prosthesis, such as a crown, a bridge or a full denture, may then be attached at the top of the abutment section.

One of the main concerns in the early development of dental implant technology was the question of whether or not an implant could withstand the intense forces which act on teeth or fixed dentures. Further developments and research, in particular in Sweden, showed that several dental units could be securely mounted on implants.

It had been known that the bone tissue in the jaw-bone were not as densely packed as other bone structures, such as for instance the forearm bones. Accordingly, a major problem associated with early implant assemblies, was the lack of absorption and deflection they provided for forces acting on the dental prostheses.

Several improvements in that respect have been suggested, such as that in U.S. Pat. No. 4,746,293 to Lundgren et al. Regarding the use of the Lundgren et al device for oral prostheses, an 0-ring of resilient material such as rubber is disposed directly below the attachment patrix for a prosthesis. The 0-ring serves as a type of shock absorber and also allows for slight deflection of the axis of the patrix with respect to the longitudinal axis of the assembly.

U.S. Pat. No. 4,772,204 to Soderberg, similar to the above Lundgren et al device, provides for two 0-rings to be disposed directly below the denture or crown, i.e. in the vicinity of the gum-line.

Several further devices have been proposed which facilitate restricted shock absorption and movement of the denture with respect to the jaw-bone. However, all such devices provide for the shock absorption means to be disposed in the vicinity of the gum-line, which leads to problems especially with the local hygiene as well as with the aesthetic appearance of the prosthesis.

SUMMARY OF THE INVENTION

It is accordingly an object of the invention to provide a dental implant and conversion assembly, which overcomes the hereinafore-mentioned disadvantages of the heretofore-known devices of this general type and which provides effective shock absorption and force vector distribution to prevent force overload on osseointegrated implant fixtures in jaw-bone tissue, and which provides mobility to the dental prosthesis supported thereon resembling that of natural teeth, while effectively sealing the implant assembly from the intrusion of bacteria.

With the foregoing and other objects in view there is provided, in accordance with the invention, in a dental implant assembly including a lower section having an implant fixture being disposed in a jaw-bone with a threaded hole formed therein; a central section having an abutment screw screwed into the threaded hole; and an upper section attached to the abutment screw, an apparatus for resiliently supporting the upper section and sealing the abutment screw against the implant fixture, comprising a cylinder surrounding the abutment screw, and a bushing surrounding the abutment screw between the cylinder and the implant fixture.

The central section thus performs two main functions, namely absorbing shocks and lateral movements of the dental prosthesis and at the same time sealing the transitional region between the implant fixture and the upper section.

In accordance with another feature of the invention, the cylinder has an inside diameter which is larger than the outside diameter of the abutment screw, defining a space therebetween, and the bushing has a substantially inverted T-shaped outer profile with a lower portion disposed between the cylinder and the implant fixture and an upper portion disposed in the space.

In accordance with a further feature of the invention, the lower portion of the bushing has a larger diameter than the upper portion. The bushing in accordance with this feature may be visualized as a combination of a cylinder and a washer, whereby the outer diameter of the cylinder is smaller than that of the washer.

In accordance with an added feature of the invention, the inside diameter of the bushing is conically tapered such that the inner diameter of the lower portion is greater than the inside diameter of the upper portion.

In accordance with an additional feature of the invention, the implant fixture has an upper surface with a profile to be engaged by a tool, and the bushing has a lower surface with a profile formed thereon, complementary to the profile on the upper surface of the implant fixture.

In accordance with again a further feature of the invention, a converter is disposed between the bushing and the implant fixture, the converter having a lower surface with a profile formed thereon, complementary to the profile on the upper surface of the implant fixture.

The converter may be used to adapt various types of implant fixtures for use with the central and upper portion of the implant assembly according to the invention. Furthermore, the converter may be used to adapt one type of upper portion to another type of implant fixture, thus making different products compatible for combined use.

With the objects of the invention in view there is also provided a second embodiment of the invention, in accordance with a concomitant feature of the invention, in a dental implant assembly for supporting a dental prosthesis including a lower section having an implant fixture being disposed in a jaw-bone with a threaded hole formed therein, and an upper section having an abutment screw screwed into the threaded hole, an apparatus for resiliently supporting the upper section and sealing the abutment screw against the implant fixture, comprising a one-piece cylinder unit including a lower cylinder section surrounding the abutment screw and an upper cylinder section to be attached to the dental prosthesis, and a bushing surrounding the abutment screw between the lower cylinder section and the implant fixture.

The above described features with regard to the cylinder, the bushing and the converter, such as the specific inside diameter of the abutment screw, the T-shaped outer profile of the bushing, the conically tapered inside opening of the bushing, the provision of a converter and the lower surface on the bushing and on the converter, respectively, which are complementary to the upper surface profile on the implant fixture, also apply to the second embodiment described in the preceding paragraph.

Other features which are considered as characteristic for the invention are set forth in the appended claims.

Although the invention is illustrated and described herein as embodied in a dental implant and conversion assembly, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF THE PREFERRED EMBODIMENTS

Figure 1:
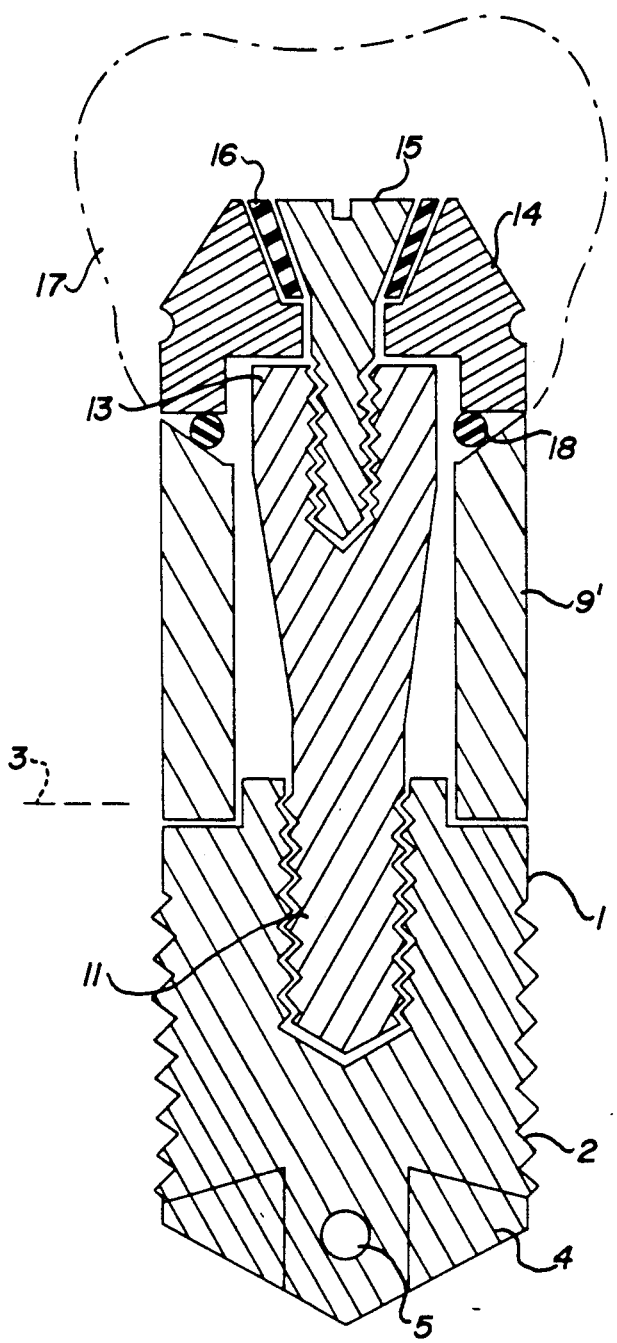
FIG. 1 is a simplified, diagrammatic, longitudinal-sectional view of a prior art implant assembly.
Figure 2:
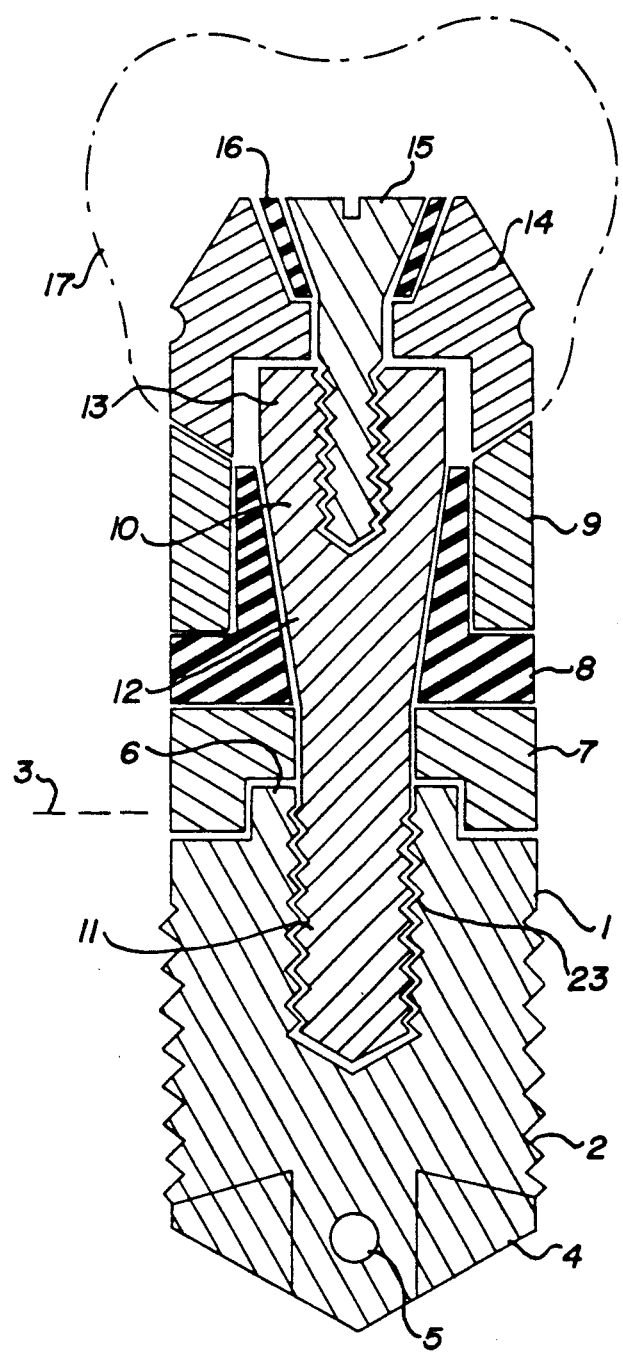
FIG. 2 is a view similar to FIG. 1 of the implant assembly according to the invention.

Referring now to the figures of the drawing in detail and first, particularly, to FIGS. 1 and 2 thereof, there is seen a screw-shaped implant fixture 1. The fixture 1 has a threaded portion 2. After a hole has been bored in the jaw-bone, the fixture 1 is screwed into the jaw-bone to an approximate level indicated by a dashed line 3. The fixture 1, which in the present state of the art is made from titanium, is implanted in the jaw-bone and, after a certain period of time, osseointegrates therewith to form a unit.

The length of the fixture 1 and its threaded portion 2 depends on the jaw-bone and the location where it is to be implanted. A wide variety of fixtures are commercially available, their lengths varying between 7 mm and 20 mm.

State-of-the-art fixtures are usually of the self-tapping type; accordingly, there is no need to provide an inner thread in the jaw-bone bore. As indicated by the cutouts 4, the fixture 1 is a self-tapping screw.

The lower portion of the fixture 1 is provided with an opening 5 into which bone tissue can grow during the osseointegration process.

The fixture 1 can be rotated with a non-illustrated tool which locks onto a nut portion 6. The portion 6 is in the form of a hex-nut which is integrated in the fixture 1. It is accessible from outside the jaw-bone and allows for rotating the fixture 1 with a fitting tool.

The fixture 1 is further provided with an axial blind hole 23 which is threaded to receive a threaded abutment screw 10. After the actual implant surgery, a non-illustrated temporary cover screw is used to close off the threaded blind hole 23 for a period of 4 to 6 months. During this period the fixture 1 is allowed to osseointegrate with the jaw-bone and the first incision in the buccal mucoperiosteum is allowed to heal.

The line 3 mentioned above shows an approximate position of the fixture with respect to the jaw-bone. The nut portion 6 may be either at the bone level, slightly lower, or even slightly higher. The latter position implies that the nut portion 6 would extend slightly into the buccal mucoperiosteum.

As seen in FIG. 1, which illustrates a device incorporating several features from different prior art devices, the central portion or abutment portion includes only one abutment cylinder 9', while the invention of the instant application, as shown in FIG. 2, includes a converter 7, a bushing 8 and an abutment cylinder 9. The crown assembly with the gold cylinder 14 rests on a resilient washer 18 or an O-ring 18 of rubber or silicon.

As seen in FIG. 2, the converter or adaptor 7 fits tightly over the nut portion 6. The converter 7 has an outer diameter substantially itentical to that of the fixture 1. However, it is possible for the converter 7 to be slightly wider or even narrower than the fixture 1.

The converter 7 may be made from the same material as the fixture, preferably titanium, a dental alloy such as gold alloy or silver palladium alloy, or even a hard plastic. The converter 7 makes it possible to use the attachment system, which will be described in the following, with different types of implant fixtures.

It is further possible to integrate the converter 7 and a resilient member or bushing 8 to form a unit. The bushing 8 is shown in FIG. 2 disposed on top of the converter 7. The bushing 8 may be made of rubber, soft nylon, silicon or an elastic plastic. The bushing 8 is shaped to receive an abutment cylinder 9, which is made of metal, preferably titanium.

The abutment screw 10, which corresponds in FIGS. 1 and 2, has a lower thread section 11, a conically tapered mid-section 12 and a head section 13. The screw 10 is screwed into the implant fixture 1. When in a locked position, the abutment screw 10 forces the bushing 8 against the inner wall of the abutment cylinder 9. The bushing 8 is also pressed downwardly against the converter 7, which in turn is forced downwardly against the implant fixture 1. Accordingly, the joints between the bushing 8 and the converter 7, and also between the converter 7 and the fixture 1, are tightly closed. This prevents the intrusion of bacteria.

Although the inner opening of the bushing 8 is shown to be conical, it is possible to use a cylindrical center opening. The latter, with an appropriate inner diameter, may ensure even better sealing characteristics, when the abutment screw 10 forces the bushing 8 against the sleeve or abutment cylinder 9.

The head section 13 of the abutment screw 10 is in the form of a hexagonal nut, comparable to the nut section 6 of the implant fixture 1. A non-illustrated tool can be applied to the head section 13 for the purpose of rotating the abutment screw 10 in order to either tighten or loosen it.

The top section of the implant assembly shown in FIGS. 1 and 2 includes a cylinder 14 and a top screw 15. The cylinder 14, which is preferably made of dental gold, is located on top of the abutment cylinder 9. The top screw 15 forces the cylinder 14 downwardly and, by applying pressure on the abutment cylinder 9, further "sandwiches" the bushing 8 between the converter 7 and the cylinder 9.

The top screw 15, which is usually a gold screw in the state-of-the-art, is shown with a slotted head for use with a regular screwdriver. An optional rubber or silicon conical washer 16 is placed between the head of the gold screw 15 and the gold cylinder 14.

As indicated by the phantom lines, a crown 17 is fitted onto the cylinder 14. The crown 17 is shown on a smaller scale than the rest of the dental implant assembly. The crown 17 may be removed by simply unscrewing the gold screw 15 and lifting the crown 17 and the cylinder 14 from the implant assembly.

Figure 3:
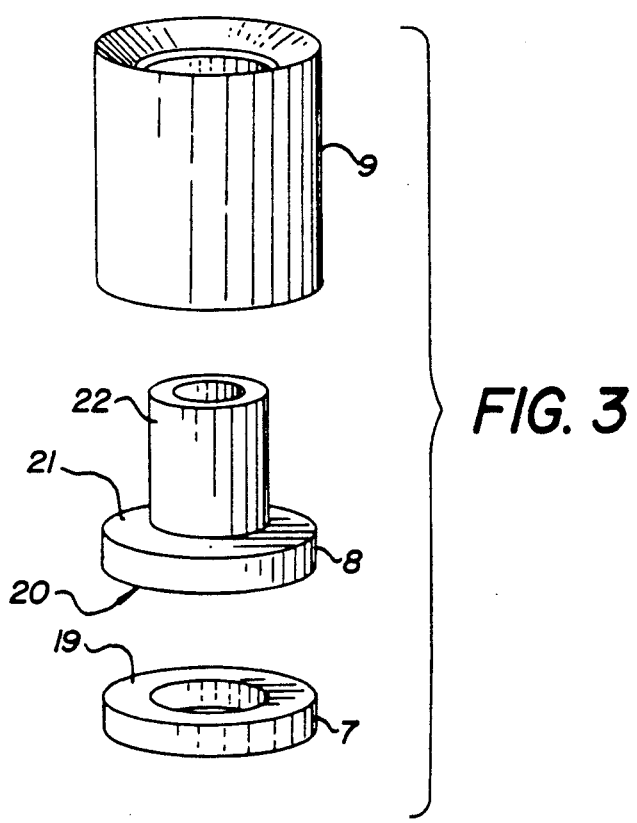
FIG. 3 is an exploded perspective view of the central abutment portion of the implant assembly according to the invention.

FIG. 3 illustrates that the converter 7 forms a top surface 19 for tight abutment with a bottom portion 20 of the bushing 8. As mentioned above, the converter 7 fits tightly over the nut portion 6 of the fixture 1.

The bushing 8 includes a washer section 21 and an inner cone section 22. The substantially flat top surface of the washer section 21 abuts tightly against the lower rim of the abutment cylinder 9. The bushing 8, furthering its shock absorption function, thus forms an effective seal against the intrusion of any kind of foreign matter, including saliva or bacteria into the joint between the abutment cylinder and the implant fixture 1.

Figure 4:
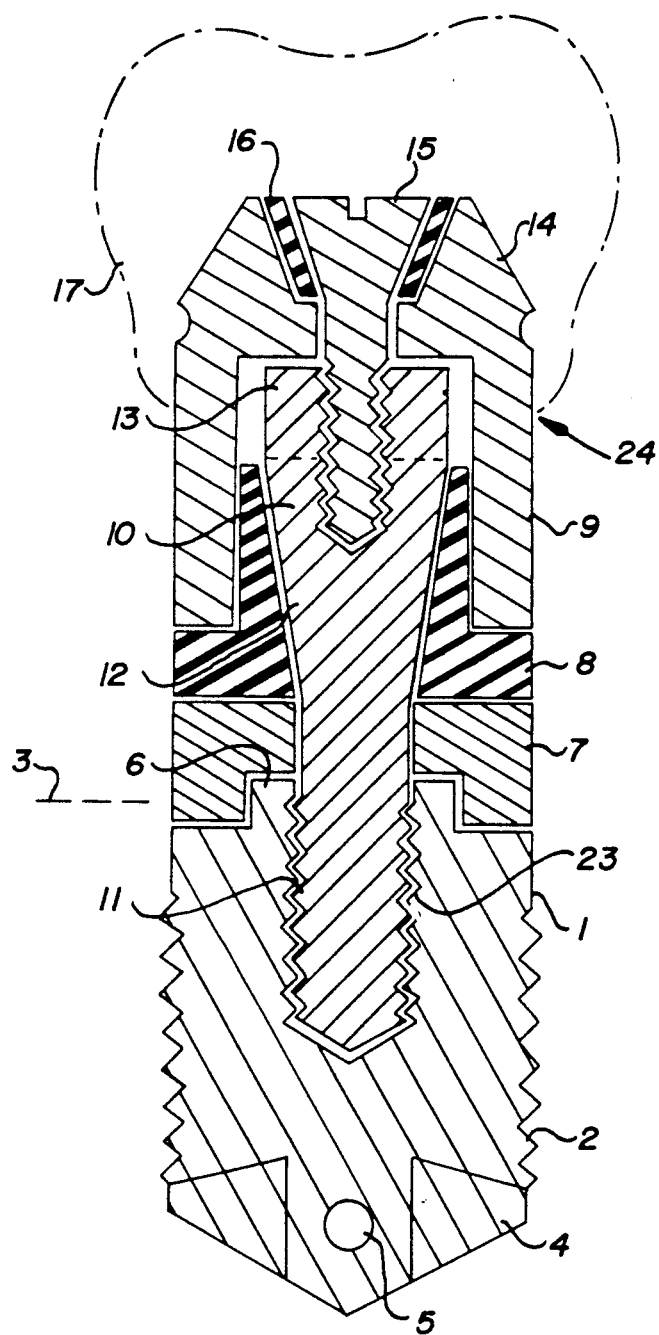
FIG. 4 is view similar to FIGS. 1 and 2 of a second embodiment of the invention.

Referring now to FIG. 4, there is seen a second embodiment of the invention, in which the cylinder 9 and the cylinder 14 are combined to form a single cylinder unit 24.

I claim:

1. In a dental implant assembly including a lower section having an implant fixture to be disposed in a jaw-bone with a threaded hole formed therein; a central section having an abutment screw screwed into the threaded hole and rigidly supported therein; and an upper section attached to the abutment screw, an apparatus for resiliently supporting the upper section and sealing the abutment screw against the implant fixture, comprising a cylinder surrounding the abutment screw, and a bushing surrounding the abutment screw separating said cylinder from the implant fixture, said bushing having means for sealing said cylinder against the implant fixture.

2. Apparatus according to claim 1, wherein said cylinder has an inside diameter being larger than the outside diameter of the abutment screw, defining a space therebetween, and said bushing has a substantially inverted T-shaped outer profile with a lower portion disposed between said cylinder and the implant fixture and an upper portion disposed in said space.

3. Apparatus according to claim 2, wherein said lower portion has a larger diameter than said upper portion.

4. Apparatus according to claim 2, wherein said inside diameter is conically tapered such that said diameter of said lower portion is greater than the inside diameter of said upper portion.

5. Apparatus according to claim 2, wherein the implant fixture has an upper surface with a profile to be engaged by a tool, and said lower portion has a lower surface with a profile formed thereon, complementary to the profile on the upper surface of the implant fixture.

6. Apparatus according to claim 2, including a converter being disposed between said bushing and the implant fixture and having a lower surface with a profile formed thereon, complementary to the profile on the upper surface of the implant fixture.

7. Apparatus according to claim 1, wherein said implant fixture has an upper surface with a profile to be engaged by a tool, and said bushing has a lower surface with a profile formed thereon, complementary to the profile on the upper surface of the implant fixture.

8. Apparatus according to claim 1, including a converter being disposed between said bushing and the implant fixture and having a lower surface with a profile formed thereon, complementary to the profile on the upper surface of the implant fixture.

9. Apparatus according to claim 1, wherein said abutment screw is directly screwed into the threaded hole.

10. In a dental implant assembly for supporting a dental prosthesis including a lower section having an implant fixture to be disposed in a jaw-bone with a threaded hole formed therein, and an upper section having an abutment screw screwed into the threaded hole and rigidly supported therein, an apparatus for resiliently supporting the upper section and sealing the abutment screw against the implant fixture, comprising a one-piece cylinder unit including a lower cylinder section surrounding the abutment screw and an upper cylinder section to be attached to the dental prosthesis, and a bushing surrounding the abutment screw and separating said lower cylinder section from the implant fixture, said bushing having means for sealing said cylinder against the implant fixture.

11. Apparatus according to claim 10, wherein said lower cylinder section has an inside diameter being larger than the outside diameter of the abutment screw, defining a space therebetween, and said bushing has a substantially inverted T-shaped outer profile with a lower portion disposed between said lower cylinder section and the implant fixture and an upper portion disposed in said space.

12. Apparatus according to claim 11, wherein said lower portion has a larger diameter than said upper portion.

13. Apparatus according to claim 11, wherein said inside diameter is conically tapered such that said diameter of said lower portion is greater than the inside diameter of said upper portion.

14. Apparatus according to claim 11, wherein the implant fixture has an upper surface with a profile to be engaged by a tool, and said lower portion has a lower surface with a profile formed thereon, complementary to the profile on the upper surface of the implant fixture.

15. Apparatus according to claim 11, including a converter being disposed between said bushing and the implant fixture and having a lower surface with a profile formed thereon, complementary to the profile on the upper surface of the implant fixture.

16. Apparatus according to claim 10, wherein the implant fixture has an upper surface with a profile to be engaged by a tool, and said bushing has a lower surface with a profile formed thereon, complementary to the profile on the upper surface of the implant fixture.

17. Apparatus according to claim 10, including a converter being disposed between said bushing and the implant fixture and having a lower surface with a profile formed thereon, complementary to the profile on the upper surface of the implant fixture.

18. Apparatus according to claim 10, wherein said abutment screw is directly screwed into the threaded hole.

* * * * *